United States Patent
Buisson et al.

(10) Patent No.: US 9,101,897 B2
(45) Date of Patent: Aug. 11, 2015

(54) PROCESS FOR THE PREPARATION OF A PULVERULENT COMPOSITION AND PRODUCT AS OBTAINED

(75) Inventors: Pierre Buisson, Lagord (FR); Claude Chesse, La Rochelle (FR)

(73) Assignee: INNOV'IA, La Rochelle (FR)

( * ) Notice: Subject to any disclaimer, the term of this patent is extended or adjusted under 35 U.S.C. 154(b) by 1621 days.

(21) Appl. No.: 12/293,280

(22) PCT Filed: Mar. 16, 2007

(86) PCT No.: PCT/FR2007/000462
§ 371 (c)(1),
(2), (4) Date: Apr. 10, 2009

(87) PCT Pub. No.: WO2007/118949
PCT Pub. Date: Oct. 25, 2007

(65) Prior Publication Data
US 2009/0312281 A1    Dec. 17, 2009

(30) Foreign Application Priority Data

Mar. 17, 2006   (FR) ...................................... 06 02383

(51) Int. Cl.
| A61K 31/7016 | (2006.01) |
| C07H 3/04 | (2006.01) |
| B01D 1/18 | (2006.01) |
| B01J 2/02 | (2006.01) |
| B01J 2/30 | (2006.01) |

(52) U.S. Cl.
CPC ............... B01J 2/02 (2013.01); A61K 31/7016 (2013.01); B01D 1/18 (2013.01); B01J 2/30 (2013.01); C07H 3/04 (2013.01)

(58) Field of Classification Search
CPC ............... C07H 3/04; C07H 1/06; B01D 1/18
See application file for complete search history.

(56) References Cited

U.S. PATENT DOCUMENTS

| 3,110,600 A | * | 11/1963 | Bok .................................. 426/71 |
| 3,716,408 A | * | 2/1973 | Nagasawa et al. ........... 127/46.1 |
| 5,307,640 A | | 5/1994 | Fawzy et al. |
| 5,415,695 A | | 5/1995 | Weterings et al. |
| 6,063,138 A | * | 5/2000 | Hanna et al. ................. 23/295 R |
| 7,785,646 B2 | * | 8/2010 | Wong ............................ 426/658 |

FOREIGN PATENT DOCUMENTS

| EP | 0 945 173 A1 | 9/1999 |
| FR | 2 838 654 A1 | 10/2003 |
| WO | WO 96/00610 | * 1/1996 ................. B01J 2/04 |

OTHER PUBLICATIONS

Electrochemistry Dictionary and Encyclopedia; "aqueous solution"; "non-aqueous solution"; three pages total; also available at http://electrochem.cwru.edu/encycl/art-a02-anodizing.htm; last viewed Mar. 23, 2012.*
"Aqueous Solution" definition, thefreedictionary.com; also available at http://www.thefreedictionary.com/p/aqueous%20solution; accessed Dec. 10, 2014.*

* cited by examiner

Primary Examiner — Shaojia Anna Jiang
Assistant Examiner — Bahar Craigo
(74) Attorney, Agent, or Firm — Young & Thompson

(57) ABSTRACT

Method of preparing a non-hygroscopic pulverulent composition, includes a step for the spray drying, without an atomization support, of an aqueous solution containing at least one initially hygroscopic product, having a glass transition temperature ranging from 10° C. to 110° C., and a cryogenic fluid, especially a food-grade cryogenic fluid, or a mixture of cryogenic fluids, particularly chosen from liquid air, nitrogen and carbon dioxide, the aqueous solution being obtained by dissolving the cryogenic fluid in an initial aqueous solution containing the initially hygroscopic product.

19 Claims, 7 Drawing Sheets

PROCESS FOR THE PREPARATION OF A PULVERULENT COMPOSITION AND PRODUCT AS OBTAINED

A subject of the present invention is a process for the preparation of a pulverulent composition, in particular a pulverulent composition of lactulose, as well as the product as obtained.

Spray drying processes are well known to a person skilled in the art. Generally, an aqueous dispersion of a substance to be dried is sprayed into a current of hot air passing through a drying chamber with recovery of the dry products obtained in powder form. The spray drying is used in the food industry for drying products such as milk, coffee, chocolate flavoured preparations, fruit juices, vegetable and animal extracts, the fermentation products and generally numerous ingredients and additives intended for applications in foodstuffs, cosmetics, pharmaceuticals or the fine chemicals sector. There are numerous spray drying processes, and are described particularly well at the site Niro®.com, in particular as regards the single-stage spray drying tower, the two-stage W-base drying tower, the multi-stage drying tower and the Filtermat®-type belt spray dryer.

However, it is accepted by a person skilled in the art that it is difficult, if not impossible, to use the spray drying technique, including in combination with the additional stages of drying by fluidization, for drying certain materials, such as certain sugars for example, and in particular if the purity of this sugar is reduced by the presence of other sugar molecules or by other components. This is the case with lactulose, in respect of which industrial syrups have lactulose contents comprised between 50% and 100% and preferably between 60 and 98%; thus, when a lactulose solution is dried by a standard spray drying process, an amorphous 'glass' very quickly forms, incorporating water. The lactulose glass particles progressively stick to the walls of the tower and the process stops of its own accord, taking account of the sticky effect generated. This hygroscopic character is found widely in carbohydrates (lactose, glucose, sucrose, fructose, sorbose, tagatose, xylose, non-limitatively, and lactulose for example), and renders the products unsuitable for many commercial applications. Other substances including in particular organic acids (citric acid, tartaric acid, malic acid, lactic acid, non-limitatively), certain fermentation derivatives (yeast extracts for example), low molecular weight protein substances (peptides, amino acids) and natural gums or those produced by fermentation can similarly adopt glass forms when spray-dried. These hygroscopic forms cannot be compressed directly.

The products considered hygroscopic, such as lactulose, have many applications in various fields. For example, lactulose is well known for its effectiveness in relation to the treatment of constipation and hepatic encephalopathy, but also for its prebiotic properties, i.e. growth activator of bifidogenic microorganisms. Also, it is known that lactulose added to a baby milk powder promotes the production of $L.$ $Bifidus$ in the infant's intestinal flora, in a similar manner to that which occurs when the infant is fed on breast milk. This demonstrates that the use of lactulose is sought in both the human or veterinary pharmaceutical field and as a food additive of a nutritional nature, and that the field of applications is very broad.

Due to its acknowledged hygroscopic character, lactulose is still used today mainly in the form of a syrup, the dry extract concentration of which is variable from 50% to 100%.

Many processes of the state of the art have been researched with the aim of obtaining lactulose in a stable powder form.

Thus, U.S. Pat. No. 5,326,405 describes a method for the preparation of crystallized lactulose by carrying out simultaneous stirring and heating of a lactulose solution in order to evaporate the water, whilst incorporating crystals until a fluid powder is obtained. The drawback of this technique resides in the discontinuous nature of the method and the difficulty of transferring the process to the industrial scale in acceptable economic conditions. It is moreover necessary to have crystals available for seeding, with the contamination risks involved and the introduction of an additional and costly stage.

U.S. Pat. No. 5,415,695 describes a process for the preparation of dry forms by evaporation of a lactulose syrup in order to reduce the water content, followed by an operation of cooling to solidification. The solid product can be ground. The method requires undertaking a rapid cooling of the lactulose solution. The drawback, apart from the aspect of the high energy consumption of the process, is the introduction of a costly additional grinding and sieving operation and resulting in the formation of fine "dusts", risking loss of product and therefore a drop in yield. The presence of fines can moreover increase the risks of cross-contamination during the production of products, and increase the problems of sticking to the walls, compacting during storage.

Document EP 0,622,374 describes a similar process leading to the formation of a crystallized lactulose trihydrate, with the above mentioned drawbacks of complexity and the cost of such processes, significantly limiting the field of applications, in particular for food applications.

International application WO 98/19684 describes a counter-current method of spray drying a lactulose solution on a fluidized bed; however in order to obtain the dry product at output it is necessary to add an absorption or gelling agent to absorb the water. Once again, the drawback resides in the discontinuous nature of the process and the necessity for the addition of foreign substances.

International application WO 00/36153 describes a method for drying a lactulose solution by using a process of drying under vacuum, the solution being heated to a high temperature under vacuum: the production of foam makes it possible to promote drying and to obtain a dry cake which is then ground to obtain a lactulose powder. The process has the drawback of working at a high temperature with the possible risks of browning associated with Maillard reactions if the lactulose solution is insufficiently purified and particularly the introduction of an additional operation of crushing sieving, with the risk of loss of materials, production of fines and the drawbacks already described.

It is important to emphasise that the powders originating from industrial lactulose syrups have a much lower glass transition temperature and particularly if the powder is not anhydrous; therefore with a water content of 3%, the lactulose powders originating from industrial syrups have a glass transition temperature comprised between 35° C. and 75° C., which leads to rapid moisture re-uptake and sticking problems.

In Paper number 046004 ASAE Annual meeting 2004, the correlations were described between glass transition and sticking point temperature of food powders considered to be difficult to dry by spraying, even unable to be dried without an atomization support; they have a low glass transition (Gt) temperatures, and are very hygroscopic in their amorphous state. During spray drying for which residence times are very short, the glass transition temperature reduces and the conversion of soluble products such as sugars and organic acids is obtained, for example to their amorphous form. In the presence of drying air which is not dehumidified, water acts as a plasticizer and progressively reduces the glass transition temperature with increasing humidity and water activity, leading to uncontrolled sticking effects in the drying installations. In order to remedy this problem, a person skilled in the art uses atomization supports which have high glass transition temperatures, such as protein isolates, maltodextrins, which are added to the solution to be dried. The relationship between glass transition temperature and water activity makes it possible to predict the stability of the powders obtained during storage.

Due to its hygroscopic properties, many attempts have been made to resolve these problems, in particular for spray drying of a solution of greater or lesser lactulose purity and greater or lesser dry matter content.

Thus, patents NE129368, 147784 and 150161 describe methods for the preparation of lactulose-based dry forms obtained by spraying, in all cases requiring the addition of atomization supports (rice flour); the drawbacks of these processes reside, on the one hand in the reduction of the lactulose concentration by weight relative to the weight of the pulverulent preparation, and in the introduction of new substances leading to extra costs and which will be found in the syrups when they are returned to solution for example, with the associated regulatory constraints.

U.S. Pat. No. 3,716,408 describes a lactulose powder with a 55% lactulose content obtained by atomization. In order to remedy the serious drawback of hygroscopic powder, it is necessary to incorporate an external agent, more particularly a Konjac powder, into the solution with the aim of allowing the drying of the mixture; the process having the drawback of the addition of an adjuvant, which may be banned for certain applications or/and regulations and which must mandatorily be stated on the labelling in the case of both a pharmaceutical and a food application.

Patent JP778565 describes a process of spray drying in order to obtain a powder with 55% lactulose concentration, but to which a protein is added to act as drying adjuvant; this powder also has well-known instability characteristics in a damp environment with the drawback of an additional adjuvant.

The purpose of the present invention is to provide a process for the preparation of a stable and non-hygroscopic pulverulent composition from a product which is originally hygroscopic. More particularly, the purpose of the present invention is to provide a process for the preparation of a non-hygroscopic and stable lactulose powder.

The present invention relates to a process for the preparation of a non-hygroscopic pulverulent composition, comprising a stage of spray drying, without an atomization support, of an aqueous solution containing at least one originally hygroscopic product, for example in liquid form, having a glass transition temperature of 10° C. to 110° C., and a cryogenic fluid, in particular a food-quality cryogenic fluid, or a mixture of cryogenic fluids, in particular chosen from carbon dioxide, nitrogen, liquid air, said aqueous solution being obtained by dissolving said cryogenic fluid in an initial aqueous solution containing said originally hygroscopic product.

The process of the present invention is characterized in that it does not include the use of a drying adjuvant.

The expression "spray drying" designates a process for drying a liquid by spraying said liquid in a current of hot air by nozzles or rotary atomizers. The drying and water transfer are carried out by entraining in the air due to the difference in vapour pressure between the droplet formed and the air at the periphery of the droplet.

The expression "atomization support" designates a substance present under its non-hygroscopic dry form such as maltodextrin, modified starch, fibres, gums and proteins, added in proportions of 2% to 75% (dry weight) into an aqueous solution containing at least one originally hygroscopic product allowing the sticky and hygroscopic character of the powder to be reduced.

The hygroscopicity of a product is defined as the affinity of said product for water. This affinity for water affects the sorption isotherms and therefore the water activity ($w_a$) and water content. These four factors ($w_a$, water content, composition and hygroscopicity) are interdependent. The hygroscopicity is responsible for the adsorption of the ambient water vapour by said product, in opposition to the desorption. The powders can be classified in five categories according to their hygroscopicity (Séchage des lactosérums et dérivés, Rôle du lactose et de la dynamique de l'eau, Pierre Schuck et al, Lait, 84 (2004) 243-268):

| Classifications | Hygroscopicity percentage or final water content after exposure to moist air at 80% residual humidity. |
|---|---|
| Non-hygroscopic | =10.0 |
| Slightly hygroscopic | 10.1-15.0 |
| Averagely hygroscopic | 15.1-20.0 |
| Hygroscopic | 20.1-25.0 |
| Very hygroscopic | >25.0 |

Galactose, the glass transition temperature of which is equal to 32° C., and tartaric acid, the glass transition temperature of which is equal to 18° C. can be mentioned as hygroscopic products.

As for lactulose, it has a glass transition temperature of 94° C.

Other hygroscopic products are given in the following table:

| Sugars | Relative hygroscopicity | Melting temperature (° C.) | Solubility in water at 60° C. (% weight/weight) | Glass transition temperature (° C.) | Sticking property (relative) |
|---|---|---|---|---|---|
| Lactose | + | 223 | 35 | 101 | + |
| Maltose | ++ | 165 | 52 | 87 | ++ |
| Sucrose | +++ | 186 | 71 | 62 | +++ |
| Glucose | ++++ | 146 | 72 | 31 | ++++ |
| Fructose | +++++ | 105 | 89 | 5 | +++++ |

Cryogenic fluid can be used for the dissolution stage, in liquid or gaseous form. Preferably, a food-quality cryogenic fluid is used.

The present invention makes it possible to produce a pulverulent preparation of lactulose, the purity of which is comprised from 50% to 100%, at a very high concentration, with improved performances in comparison to those of the pulverulent preparations of lactulose of the prior art, making it possible to obtain powders with novel and surprising physical properties: they have a very high preservation stability in the open air without compacting, demonstrating the absence of the characteristic of hygroscopicity, in contrast to the lactulose powders of the prior art. Simply touching a hygroscopic lactulose powder leaves an immediate mark on the finger due to the instantaneous adherence caused by heating of the powder in contact with the finger. The present invention makes it possible to produce a powder which has an inertia of several tens of seconds to the temperature of the skin, which is a very substantial advantage in the case of handling sachets of lactulose powder for example.

The present invention also makes it possible to supply a stable lactulose powder without the addition of atomization supports to the solution, from a lactulose solution which can have a variable degree of purity, comprised between 50% and 98%, in the more usual and most difficult cases, but also purities greater than 98% or less than 50%.

The present invention surprisingly makes it possible to obtain lactulose powders which are perfectly white, bringing an additional advantage of the complete absence of influence on colouring, during the production of novel dry preparations based on lactulose; this property can be compared to the beige colour of the powders of the prior art.

The present invention also makes it possible to supply a high-concentration lactulose powder having excellent wettability properties and rate of instant solubilization.

The present invention also makes it possible to supply a lactulose powder having a minimum of fines, this absence of dusts avoiding all the risks of airborne contamination during use of the product, and reducing any risks of allergies by inhalation of dusts of the product.

The present invention also makes it possible to supply a lactulose powder, the variable degree of purity of which can be comprised between 50% and 98% in the more usual and most difficult cases, but also for purities greater than 98% or less than 50%, directly compressible, having flow properties suitable for compression.

A person skilled in the art knows the work carried out which make it possible to explain the effects of powder stickiness essentially associated with the characteristics of hygroscopicity and themoplasticity of the powders; it is known that at a temperature comprised between 75° C. and 100° C., lactulose powder has a very high thermoplasticity.

Glass transition is a change in the state of a substance under the effect of temperature, involving significant variations in its mechanical properties. Glass transition is characterized by the transition temperature: above this temperature the product has a plastic structure (viscoelastic state); below this temperature the product has a structure called vitreous (solid state) and has the behaviour of an elastic solid product.

The glass transition temperature of pure anhydrous lactulose is 90° C. to 95° C.; the latter decreases very rapidly from 10° C. to 40° C. as a function of the water content of the powder in equilibrium with air, for vapour pressures of this air close to 5%; it also decreases with purity and thus describes a temperature range in which the product has thermoplasticity properties (see "Notion de transition vitreuse appliquée au séchage par pulvérisation de solutions glucidiques", Laurence Busin, Pierre Buisson, Jacques Bimbenet, Sciences de l'aliment 16 (1996) 443-459).

This model does not describe the kinetics of the phenomenon of permanent transfer of heat and water; if the glass transition temperature for pure anhydrous lactulose is 90° C. to 95° C., the glass transition temperature of a technical lactulose solution obtained industrially, moreover containing lactulose from other sugars (lactose, galactose, fructose, etc), is necessarily lower.

Surprisingly, it has been noted that for a humidity of less than 2%, there was a preferential stabilization zone of the lactulose powder comprised from approximately 50° C. to approximately 85° C., preferably approximately 65° C. to approximately 80° C., and in particular approximately 65° C. to approximately 75° C., leading to the elimination of all the stickiness effects in the cyclones of the spraying tower, by controlling spraying of the solution in a current of hot air under controlled enthalpy conditions.

In an unexpected and very surprising fashion, a sudden change was noted to a definitively stable state of lactulose particles powder having a high thermoplasticity, when the particles were subjected to a sub-cooling, by the rapid expansion of a food-quality cryogenic fluid such as for example carbon dioxide or nitrogen or liquid air and preferably carbon dioxide injected at a pressure comprised between $10^5$ Pa and $5\times10^6$ Pa, and preferably between $5\times10^5$ Pa and $10\times10^5$ Pa, the carbon dioxide being on the one hand in liquid form in the solution and on the other hand in gaseous form. However, the phenomenon is improved even more by the presence of molecules of carbon dioxide dissolved in the solution. In fact, during expansion of the cryogenic fluid dissolved during spraying, the frigories are contributed by the latent heat of the change of state, i.e. 64 frigories per kg of liquid carbon dioxide (38 frigories per kg for nitrogen), and by the sensible heat of the carbon dioxide gas leading to an availability of approximately 100 frigories per kilogram of carbon dioxide gas. This injection allows the powder to stabilize in the drying tower in temperature zones from 20° C. to 100° C.

Thus, the present invention also makes it possible to obtain a lactulose powder, by carrying out continuous overdrying of the powder obtained by subjecting it to an instantaneous sub-cooling in situ by controlling low temperatures ranges comprised between 20° C. and 100° C., and preferably between 40° C. and 75° C.

The present invention also makes it possible to obtain a lactulose powder under the conditions described above, while subjecting the lactulose particles to a rapid expansion of a food-quality refrigerant (carbon dioxide or nitrogen for example, and preferably carbon dioxide) which does not contribute additional moisture, which otherwise would result in an a reversibility of the change of state and a return to an unstable thermoplastic condition.

One of the other aspects of the present invention is also, as under the conditions described above, to carry out the injection of $CO_2$ under pressure in the gaseous or liquid state (carbon dioxide or nitrogen gas for example, non-limitatively) in the pre-heated solution, making it possible, in a surprising fashion, to allow the heated carbonated solution to be sprayed at very high concentrations of the solutions and having very high critical viscosities up to 2000 centipoises, while the critical viscosities usually known and used by a person skilled in the art during the drying by spraying in a current of hot air, are situated between 50 to 200 centipoises. This higher rate of concentration has the double advantage of, on the one hand, reducing the humidity of the equilibrium air for drying, i.e. the quantity of water in the air retrieved during the adiabatic transfer, and on the other hand, very substantially increasing productivity and thus the economic benefit of the process.

Thus, while all the tests and experiments conducted both on single-stage spray drying tower with rotary atomizer (NIRO Minor Mobile® tower) and a multi-stage spray drying tower (Tour NIRO MSD 20®) equipped either with a single high-pressure nozzle or a two-fluid nozzle, or on a two-stage W-base tower with nozzle have resulted in rapid stickiness being observed with no possibility of operating in a stabilized regime, the present invention has demonstrated that it was possible to obtain on each of these spray drying towers and spray drying towers configuration: single-stage tower, tower called multi-stage equipped either with a high-pressure single spray or a two-fluid nozzle, W-base two-stage spray drying tower with nozzle, tower called "cigar" or tall form, spray drying tower of the Filtermat® type equipped with an integrated belt dryer at the base, on an industrial scale, and under economic conditions responding to market demands, the present invention has demonstrated that it was possible to obtain a stable lactulose powder, the lactulose purity of which can be comprised between 50% and 100% expressed by weight of lactulose the hygroscopicity of which is substantially reduced, without using costly industrial processes or providing a drying support additive or atomization support (dilution factor), or without the need to carry out a costly purification of the lactulose solution used. The invention also relates to the process of spray drying of a concentrated liquid technical lactulose solution having a substantial viscosity, which can be comprised between 50 and 2000 centipoises, solution previously heated for approximately 1 to approximately 10 minutes, preferably from approximately 2 to approximately 5 minutes, at a temperature of approximately 20° C. to approximately 75° C., and in which a cryogenic fluid in liquid or gaseous form, preferably carbon dioxide, has been dissolved under pressure. In the framework of carbon dioxide use, spraying of the hot carbonated solution is carried out concomitantly with an anti-agglomeration agent chosen from the range of anti-agglomeration agents known to a person skilled in the art, and preferably of the colloidal silica type.

According to an advantageous embodiment, the preparation process of the invention is characterized in that the spray drying stage is accompanied by a primary stabilization resulting from the cooling of the pulverulent composition obtained during the spray drying stage, this cooling being caused by the expansion of the cryogenic fluid dissolved in the initial aqueous solution.

According to another advantageous embodiment, the preparation process of the invention is characterized in that the cooling of the pulverulent composition obtained during the spray drying stage takes place within a temperature range lower than the glass transition temperature of the hygroscopic product, and in that the water content of said pulverulent composition obtained on completion of said stage is less than approximately 7%, and is in particular approximately 1% to approximately 4%.

A preferred preparation process according to the present invention is characterized in that the originally hygroscopic product is chosen from organic products the average molecular mass of which is less than approximately 1,000 Da, in particular comprising at least 50% by weight of glucides, such as lactulose, fructo-oligosaccharides, galacto-oligosaccharides, fructose, maltose, lactose, saccharose, glucose, inulin or mixtures of these, polyols such as sorbitol, maltitol or xylitol, honey-based compositions, products derived from the extraction of lactose, lactoserum or its derivatives, mixtures of sugars and sweeteners, such as mixtures of fructo-oligosaccharides and aspartame, acesulphame or rhamnose.

Among the hygroscopic products, there can also be mentioned extracts of hygroscopic plants such as lucerne serum obtained after protein extraction, the cytoplasmic content of fresh plant cells, artichoke extracts or polyphenolic plant extracts (in particular grape or apple), mixtures combining one or more probiotics (and in particular those of the *Lactobacillus* and *Bacillus* families), and one or more active ingredients of nutritional interest and in particular prebiotics (in particular lactulose, fructo-oligosaccharides, rhamnose), polyunsaturated fatty acids (such as extracts of fish oil rich in ω3), polyphenols (in particular catechols and grape seed extracts), and yeast extracts.

According to an advantageous embodiment, the present invention relates to a process for the preparation of a pulverulent lactulose composition comprising a spray drying stage of an aqueous lactulose solution and a food-quality cryogenic fluid, in particular chosen from carbon dioxide, nitrogen, liquid air or a mixture of these, said aqueous solution being obtained by the dissolution of said food-quality cryogenic fluid in an initial aqueous solution containing lactulose.

The present invention relates to a preparation process as defined above, in which the spray drying stage is preceded by a stage of simultaneous spraying of an anti-agglomeration agent and aqueous solution containing the originally hygroscopic product, in particular lactulose, and the food-quality cryogenic fluid.

The expression "anti-agglomeration agent" designates a water-absorbent substance, generally in powder form, added to foodstuffs to prevent their agglomeration or maintain their fluidity.

Within the framework of the present invention, the anti-agglomeration agent does not perform the role of an atomization support.

According to an advantageous embodiment, the process of the invention is characterized in that the concentration of anti-agglomeration agent is less than approximately 0.5%, and varies preferably from approximately 0.1% to approximately 0.3% by weight of dry extract of the anti-agglomeration relative to the weight of dry extract of the non-hygroscopic pulverulent composition, in particular lactulose.

According to an advantageous embodiment, the process of the invention is characterized in that the anti-agglomeration agent is chosen from: colloidal silica, silicates, magnesium carbonate, calcium, talc and phosphate.

According to a preferred embodiment, the present invention relates to a preparation process as defined above, characterized in that the spray drying stage is carried out with hot air at a temperature of approximately 100° C. to approximately 250° C., preferably approximately 115° C. to approximately 150° C.

The present invention also relates to a preparation process as defined above, characterized in that the initial aqueous solution containing the originally hygroscopic product, in particular lactulose, is at a temperature of approximately 50° C. to approximately 85° C., preferably approximately 65° C. to approximately 80° C.

A preferred preparation process according to the present invention is characterized in that the initial aqueous solution containing the originally hygroscopic product, in particular lactulose, has a concentration of dry matter of approximately 20% to approximately 80% by weight of dry matter relative to the weight of the initial aqueous solution, and preferably approximately 60% to approximately 70%.

The present invention also relates to a preparation process as defined above, characterized in that the initial aqueous solution containing the originally hygroscopic product, in particular lactulose, contains approximately 20% to approximately 100%, in particular approximately 50% to approximately 100%, and preferably approximately 60% to approximately 80% by weight of hygroscopic product relative to the total weight of dry matter.

According to a preferred embodiment, the cryogenic fluid is at a pressure comprised from approximately $10^5$ Pa to approximately 20×10⁵ Pa, preferably from approximately 4×10⁵ Pa to approximately 12×10⁵ Pa.

A particularly advantageous preparation process according to the invention is characterized in that the aqueous solution containing the originally hygroscopic product, in particular lactulose and the cryogenic fluid is sprayed at a pressure of approximately 2×10⁶ Pa to approximately 2×10⁷ Pa.

The present invention relates to a preparation process as defined above, characterized in that the stage of spray drying and primary stabilization resulting in a sprayed mixture is followed by a stage of secondary stabilization by cooling said sprayed mixture by secondary air, partially dehydrated, in particular introduced as a counter-courant to the hot drying air.

The present invention thus consists of combining a system of drying the air by a Munters Dessicant Rotor type system, making it possible to improve the productivity of the process by making air available which is dehydrated to 1 g of water per kg of air, although this system is not mandatory for carrying out the process, a system of partial drying of the air by a cooling battery making it possible to reach adequate residual water content rates of 4 to 5 g of water per kg of air.

According to a preferred embodiment, the process of the invention is characterized in that the non-hygroscopic pulverulent composition, in particular the pulverulent lactulose composition, obtained at the outlet of the spray drying stage and primary stabilization and the stage of secondary stabilization carried out in a spraying tower, is introduced into one or more cyclone(s).

The process of the present invention is also characterized in that the non-hygroscopic pulverulent composition, in particular the pulverulent lactulose composition, is collected at the base of the spraying tower in microgranulated powder form, the average grain size of which can vary from approximately 100 µm to approximately 500 µm.

The process of the present invention is also characterized in that the non-hygroscopic pulverulent composition, in particular the pulverulent lactulose composition, is collected at the outlet of one of the cyclones.

The present invention also relates to a process as defined above, characterized in that the aqueous solution containing at least one originally hygroscopic product, in particular lactulose, and a cryogenic fluid is co-dried by spraying with a hygroscopic substance in powder form.

A technology exists called spray drying and/or co-drying combining one or more injections of dry forms with the spray drying of liquids, which makes it possible to produce directly-compressible powders of pure ingredients or mixtures of ingredients, such as sugars, mineral and vitaminized food additives. It is possible for example to envisage the spraying of a lactulose solution combined with the injection of a pure lactulose powder or in combination with other sugars having prebiotic properties (fructo-oligosaccharides, fructose, lactose), gum arabic, inulin and prebiotic-probiotic mixtures (lactulose powders, lactic bacteria, yeasts). This technology has the advantage of obtaining direct-compression homogenous powders. Direct compression is even more beneficially used as it makes it possible to obtain solid forms (tablets, caplets, lozenges) without the use of binders or an additional granulation stage.

According to an advantageous embodiment, the process of the invention is characterized in that the hygroscopic substance in powder form is chosen from organic products the average molecular mass of which is less than approximately 1,000 Da, in particular comprising at least 50% by weight of glucides, such as lactulose, fructo-oligosaccharides, fructose, saccharose, glucose or mixtures of these, polyols such as sorbitol, maltitol or xylitol, honey-based compositions, products derived from the extraction of lactose, lactoserum or its derivatives, mixtures of sugars and sweeteners, such as mixtures of fructo-oligosaccharides and aspartame, acesulphame or rhamnose.

Among the hygroscopic products, there can also be mentioned extracts of hygroscopic plants such as lucerne serum obtained after protein extraction, the cytoplasmic content of fresh plant cells, artichoke extracts or polyphenolic plant extracts (in particular grape or apple), mixtures combining one or more probiotics (and in particular those of the *Lactobacillus* and *Bacillus* families), and one or more active ingredients of nutritional interest and in particular prebiotics (in particular lactulose, fructo-oligosaccharides, rhamnose), polyunsaturated fatty acids (such as extracts of fish oil rich in ω3), polyphenols (in particular catechols and grape seed extracts), and yeast extracts.

The present invention also relates to a continuous preparation process of a non-hygroscopic pulverulent composition, said process being characterized in that it comprises the following stages:

a stage of heating an initial aqueous solution containing an originally hygroscopic product, in particular lactulose, having a glass transition temperature of 10° C. to 110° C., at a temperature of approximately 50° C. to approximately 85° C., preferably from approximately 65° C. to approximately 80° C., in order to obtain a heated initial aqueous solution, a stage of dissolution of a cryogenic fluid, in particular a food-quality cryogenic fluid or a mixture of cryogenic fluids, in said heated initial aqueous solution, said cryogenic fluid being in particular chosen from carbon dioxide, nitrogen or liquid air, and being at a pressure comprised from approximately 10⁵ Pa to approximately 20×10⁵ Pa, preferably approximately 4×10⁵ Pa to approximately 12×10⁵ Pa, in order to obtain an aqueous solution containing said hygroscopic product and a cryogenic fluid, a stage of simultaneous spraying of an anti-agglomeration agent and the aqueous solution containing said hygroscopic product and a cryogenic fluid, in order to obtain a sprayed mixture, a spray drying stage of said sprayed mixture with hot air at a temperature of approximately 100° C. to approximately 250° C., preferably approximately 115° C. to approximately 150° C., in particular in a spraying tower, in order to obtain a hygroscopic powder, partially dried and not stabilized, and primary stabilization, corresponding to a cooling and an instantaneous cooling by expansion of the cryogenic fluid of said partially dried and not stabilized hygroscopic powder, in order to obtain a composition of said hygroscopic product in the form of a non-hygroscopic stabilized powder, a stage of secondary stabilization of the non-hygroscopic stabilized powder obtained in the previous stage, corresponding to a cooling in partially dried air.

The present invention also relates to a preparation process as defined above, characterized in that the originally hygroscopic product is lactulose.

The present invention thus makes it possible to produce powders of improved bacteriological quality by the observed bacteriostatic effect associated with the presence of the cryogenic fluid.

The present invention also relates to a non-hygroscopic pulverulent composition as obtained by the process as defined above.

The present invention also relates to a non-hygroscopic pulverulent composition of lactulose as obtained by the process as defined above, optionally in a mixture with products having nutritional and/or therapeutic properties.

The present invention also relates to a non-hygroscopic pulverulent lactulose composition which is not sticky in a temperature range of approximately 10° C. to approximately 45° C., in particular at the temperature of approximately 20° C. to approximately 38° C., having a water content less than approximately 7%, and in particular approximately 1% to approximately 4%.

The non-sticky character of the pulverulent lactulose composition of the invention can be verified by the tests described in the article by Papadakis and Bahu, "The sticky issues of drying", in *Drying Technology*, 10(4), 817-837 (1992).

The pulverulent compositions of lactulose of the invention can be redissolved in water.

The present invention makes it possible to provide a process of spray drying a lactulose solution which allows the production of pulverulent compositions with a high concentration of lactulose without the addition of a support, starting from concentrated technical solutions of lactulose originating from production plants, having novel and surprising physical properties: these compositions no longer have a hygroscopic character and the immediate instability of the powders of the state of the art, and have in comparison a remarkable stability in ambient air storage conditions; moreover they offer excellent flowability and wettability properties. A further subject of the invention resides in the novel fact that the powders obtained can be compressed directly, allowing tablets, lozenges and caplets to be produced without undergoing an additional granulation phase.

LEGEND OF THE FIGURES

FIG. 1

Circle A represents the initial aqueous solution containing at least one originally hygroscopic product; rectangle (2) represents a heater; circle B represents the introduction of the cryogenic fluid or a mixture of cryogenic fluids and rectangle (3) represents the dissolution stage of said cryogenic fluid or said mixture of cryogenic fluids into said initial aqueous solution, in order to obtain an aqueous solution containing at least one originally hygroscopic product and a cryogenic fluid or a mixture of cryogenic fluids. Rectangle (4) represents a high-pressure pump used to spray said aqueous solution into the spraying tower (1) via one or more nozzles (5). Circle C represents the spraying of the anti-agglomeration agent via a powder dosimeter (6).

Circle D represents the introduction of hot air (temperature from 100° C. to 250° C.) for the spraying stage, via a fan (7).

Circle E represents the introduction of the secondary air, partially dehydrated (temperature from 100° C. to 250° C.), via a fan (8).

Rectangle (9) represents a cyclone; circle F represents the recovery of the final product by the cyclone, i.e. the non-hygroscopic pulverulent composition, and circle G represents the evacuation of the air from the cyclone outlet.

Rectangle (10) represents an external vibrated fluidized bed; circle H represents the recovery of the final product at the outlet of said fluidized bed, i.e. the non-hygroscopic powdery composition.

Circle I represents the addition in the spraying zone of a hygroscopic substance in powder form and rectangle (11) corresponds to the injection device constituted principally by a powder dosimeter.

Figure 6A:
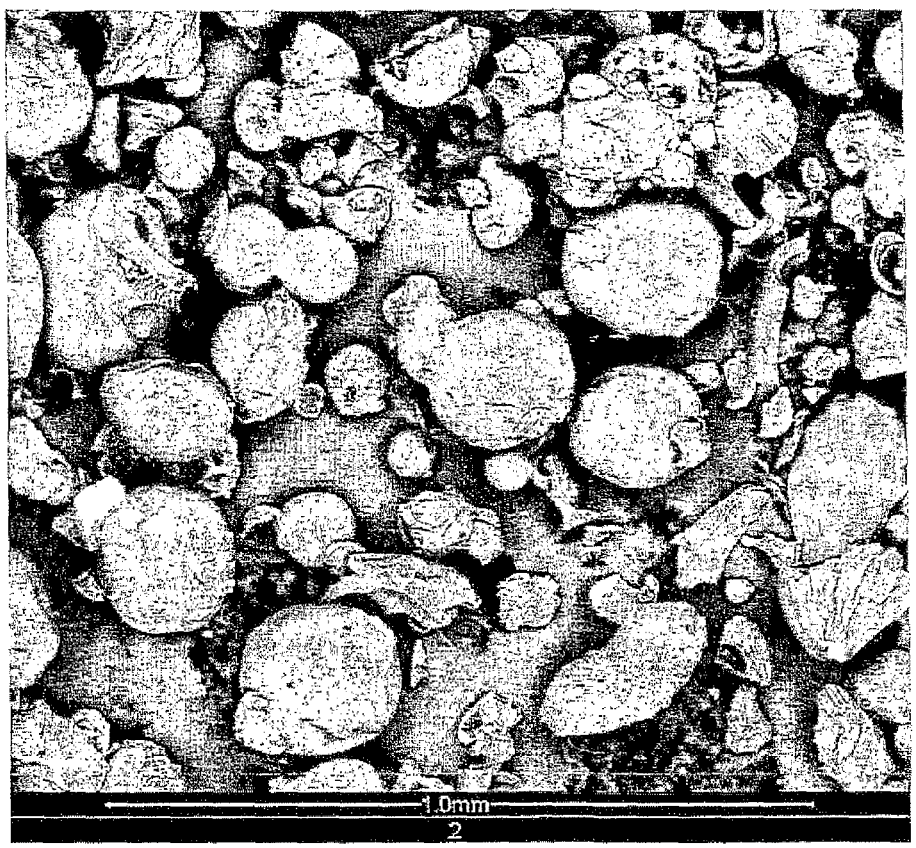

FIG. 6A represents a shot of a sample product from Example 2 of the invention (see below) of lactulose powder (enlarged 200 times). A high dispersion of the completely spherical particles of a greater size than sample A is noted. The particles have characteristic ribs.

Figure 6B:
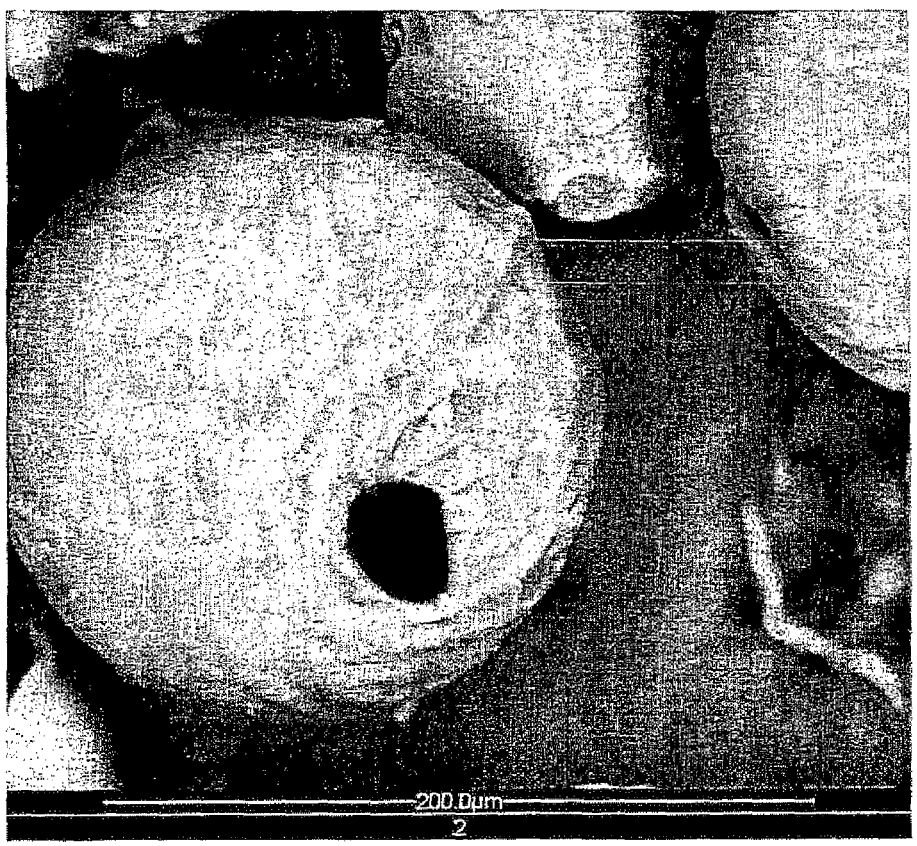

FIG. 6B represents a shot of a sample product from Example 2 of the invention of lactulose powder (enlarged 500 times). The unitary particles are spherical but of a greater size than sample A. The particles have a characteristic ribbed and inflated state, with a more marked presence of the characteristic degassing orifice of spray drying seen on the particle surface.

Figure 7:

FIG. 7 represents a particle enlarged 500 times with a ribbed surface state with a characteristic element of the degassing orifice in the form of a "sunspot" with brown lines in the form a star.

EXAMPLES

Example 1

Multi-Stage Spray Drying in a Single-Stage Tower of Modified Configuration

The equipment used in this example is a multi-stage spray-drying tower (1) (see FIG. 1), the originality of the process of which is preferably to use the tower in single-stage modified configuration. The drops formed during spraying of the lactulose solution are dried in the spraying chamber by hot air, the temperature of the incoming air being fixed at 116° C.

In this example, the cryogenic fluid is carbon dioxide.

A lactulose solution the lactulose purity of which is 70% expressed by weight of lactulose in relation to the weight of dry material, and the concentration of which as dry solution extract is 64% expressed by weight of dry material in relation to the weight of the solution, is transferred at a rate of 140 kg/h by a booster pump into a hot-water heat exchanger (2) in order to reach a temperature of 61° C. and undergoes continuous carbonation (3), the pressure of the carbonated mixture being 10 bars, before being sprayed using a high-pressure pump (4) at a pressure of approximately 200 bars ($2 \times 10^7$ Pa) via a pipe (5) with a single-fluid nozzle. Anti-agglomeration agent (6), preferably a colloidal silica, is continuously dosed at a level of 0.2% expressed by weight of silica to the weight of the dry solution extract, by injection close to the spraying zone.

The temperature of the fluidized bed is adjusted to keep the powder at a temperature of 20° C.

The temperature of the outlet air is chosen to be 75° C.; this supply of secondary air (8) is partially desaturated by a counter-current glycolated water cooling battery system, the air obtained having a residual humidity of 5 g of water per kg of air.

The air is recovered from the final powder under cyclone by choosing a dense phase conveying system and the powder is recovered by dense phase conveying.

Flodex™ Test to Determine the Flow Index of a Powder

The Flodex™ flow index is equal to the diameter of the orifice of the smaller disk through which the powder passes three times consecutively (equipment Hansen Research Corporation).

The flow is then determined according to following scale as a function of the flow index found.

| Flow index in mm | 4-7 | 8-12 | 14-18 | 20-26 | 28-34 |
|---|---|---|---|---|---|
| Flow | | Excellent | Good | Average | Reasonable | Poor |

Wettability Test

Wettability is the ability of a powder to be wetted. It corresponds to the time necessary (in seconds) for a certain quantity of powder to be penetrated in water through its free surface at rest.

Operating Method 100 ml of water is poured into a beaker and a funnel (made of antistatic material) is placed such that it is supported on the upper edge of the beaker. The temperature of the water is controlled (20° C.±2° C.).

The lower opening of the funnel is then closed and the quantity of weighed powder (the quantity of sample intended for analysis must correspond to the concentration of the powder in the water in which the given product is going to be used) is placed around the closing device. Finally, the closing device is removed and the time taken for all the powder to be wetted is measured.

The characteristics of the powders produced according to Example 1 are given in Table 1.

TABLE 1

| Moisture content of the finished product | 2% |
|---|---|
| Bulk density | 300 g/l |
| Flow (flowdex) | 20 |
| Water activity Wa | 0.206 |
| D(v, 0.5) | 40 μm |
| Average grain size by laser | |

In this case it should be remembered that the bulk density designates the measured density of the powder; therefore it relates to the ratio between the mass of the powder and the volume occupied by the powder.

Example 2

Multi-Stage Spray Drying in a Single-Stage Modified Configuration Tower

Figure 1:
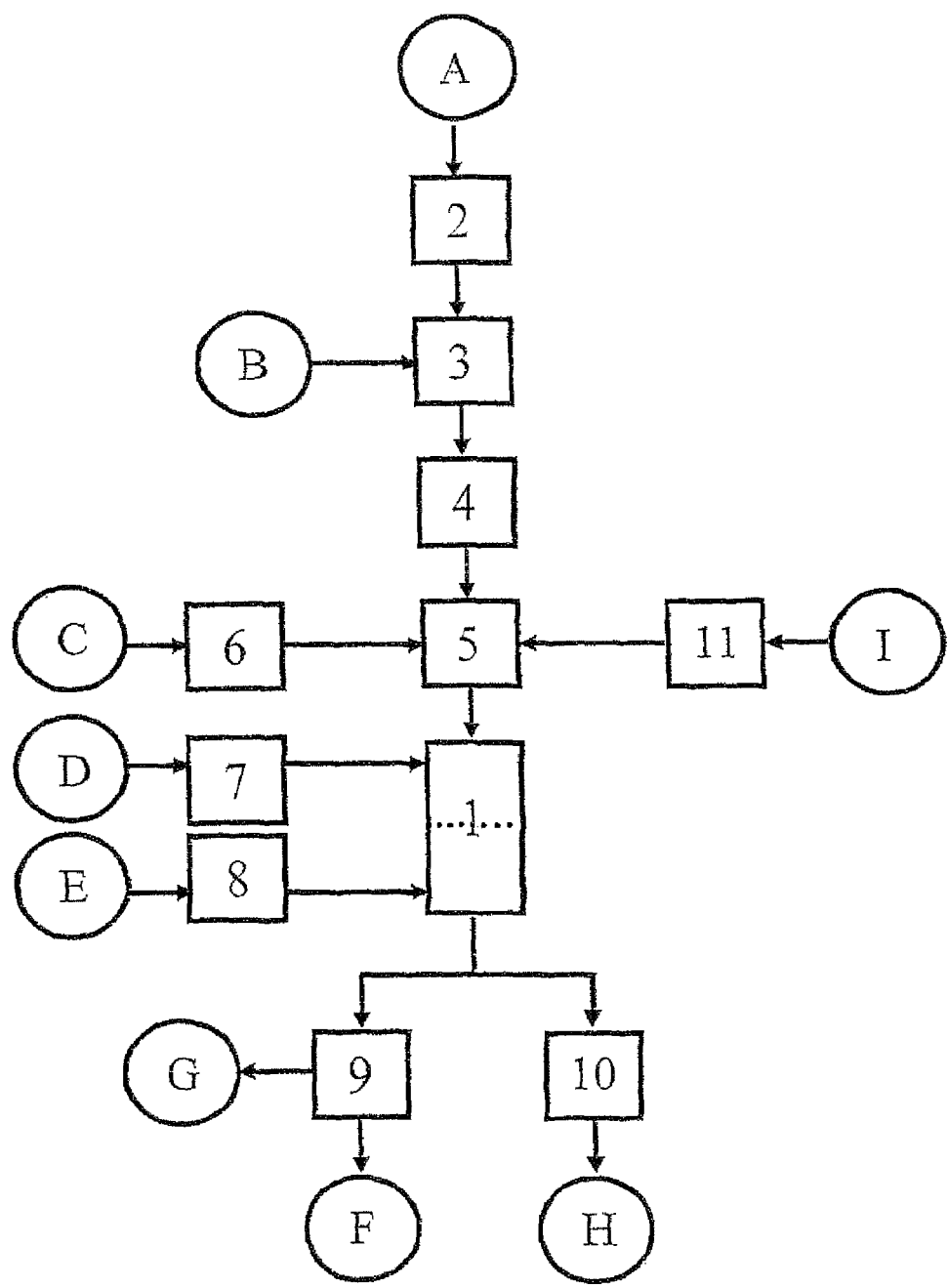
Figure 2:
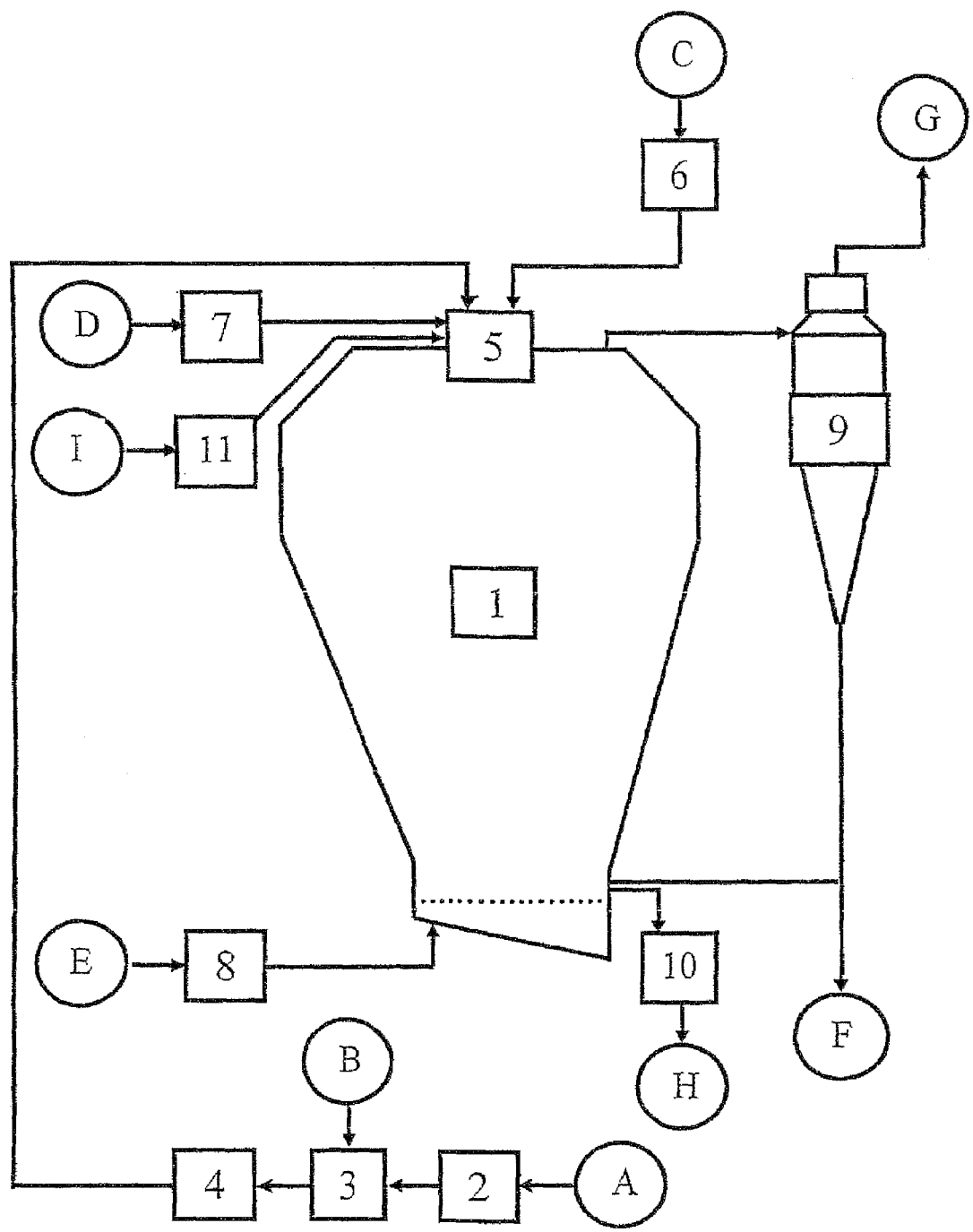
FIG. 2 is a schematic diagram of the process of the invention, implemented in a multi-stage spraying tower. Circles A, B, C, D, E, F, G, H and I, as well as rectangles (1) to (11), have the same meaning as that indicated in FIG. 1.
Figure 3:
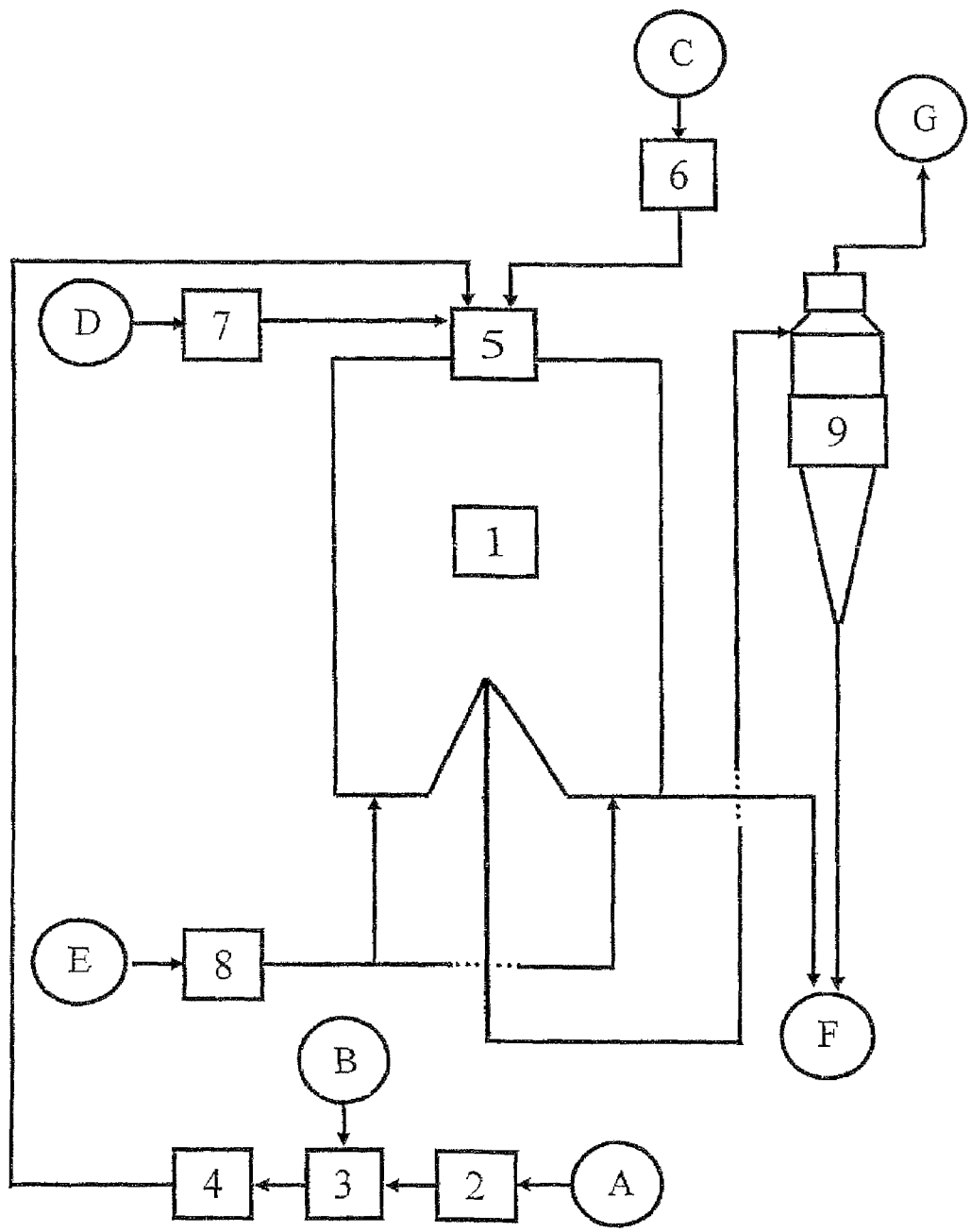
FIG. 3 is a schematic diagram of the process of the invention, implemented in a W-base spraying tower. Circles A, B, C, D, E, F and G, as well as rectangles (1) to (9), have the same meaning as that indicated in FIG. 1.
Figure 4:
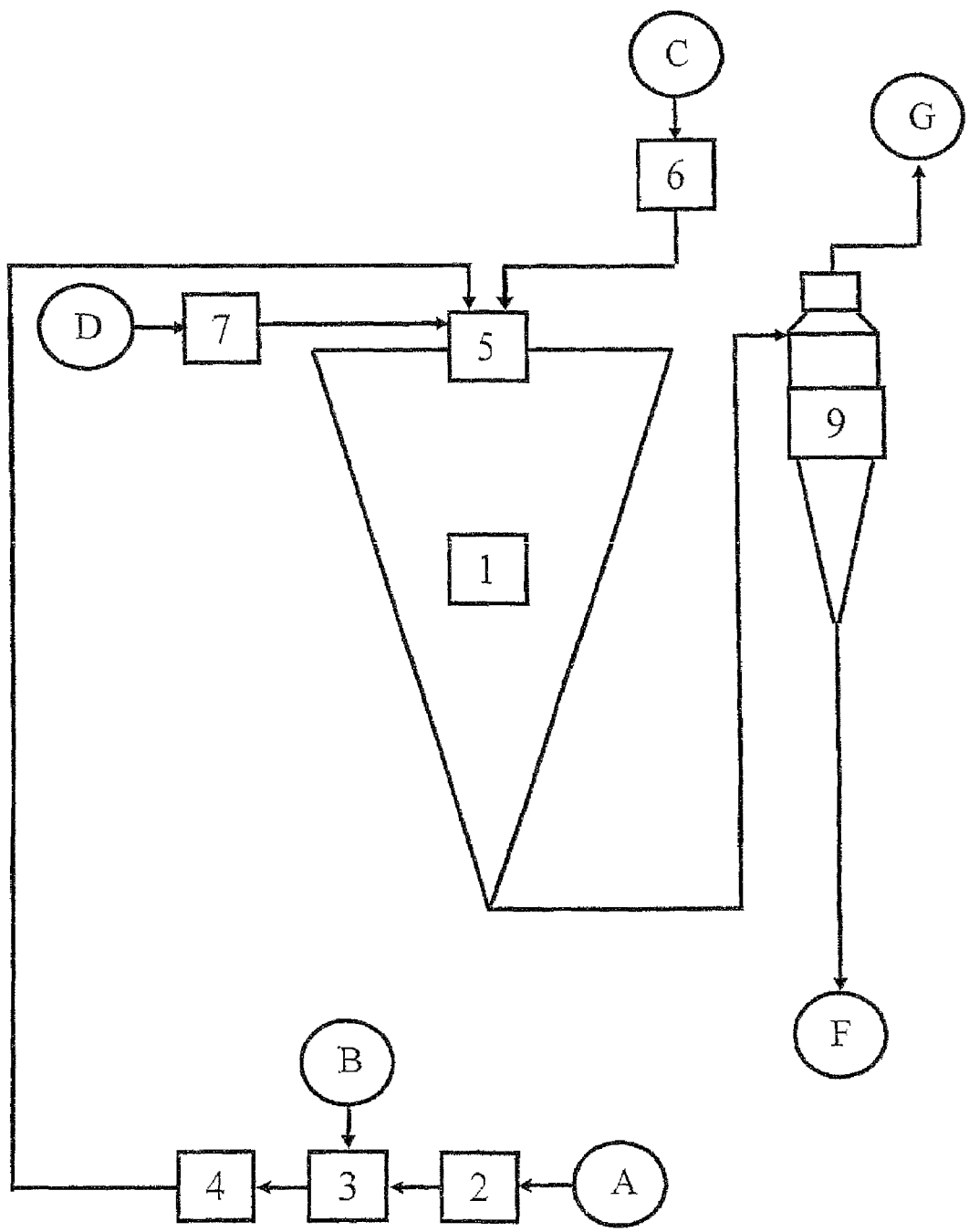
FIG. 4 is a schematic diagram of the process of the invention, implemented in a single-stage spraying tower. Circles A, B, C, D, F and G, as well as rectangles (1) to (7) and (9), have the same meaning as that indicated in FIG. 1.
Figure 5A:
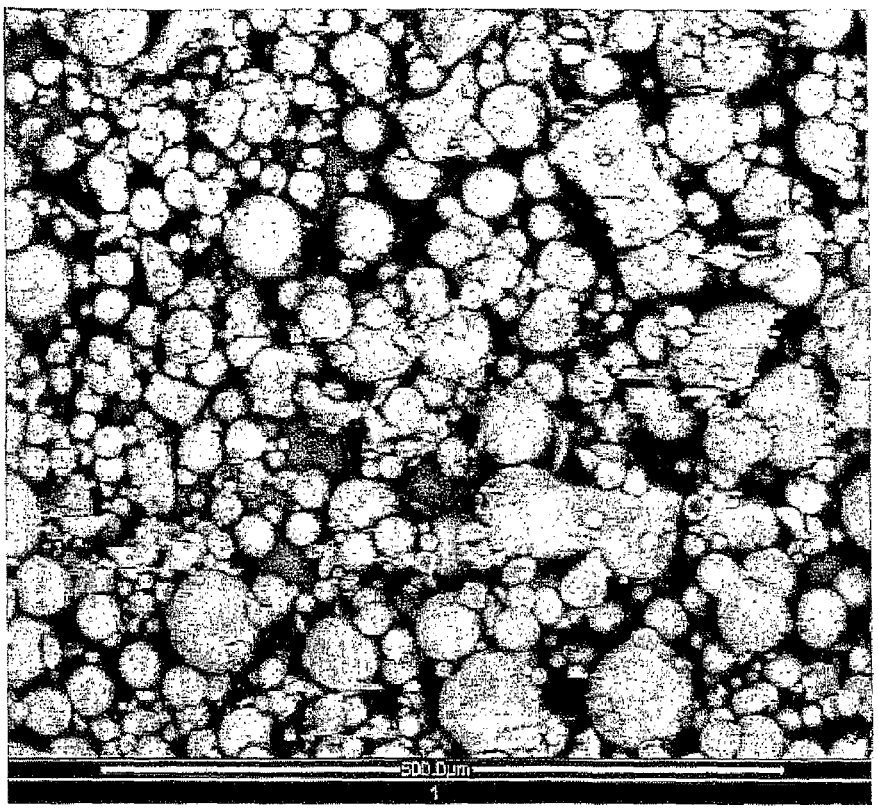
FIG. 5A represents a shot of a sample product A of lactulose powder not using the process of the invention (enlarged 200 times). A high dispersion of the completely spherical particles is noted.
Figure 5B:
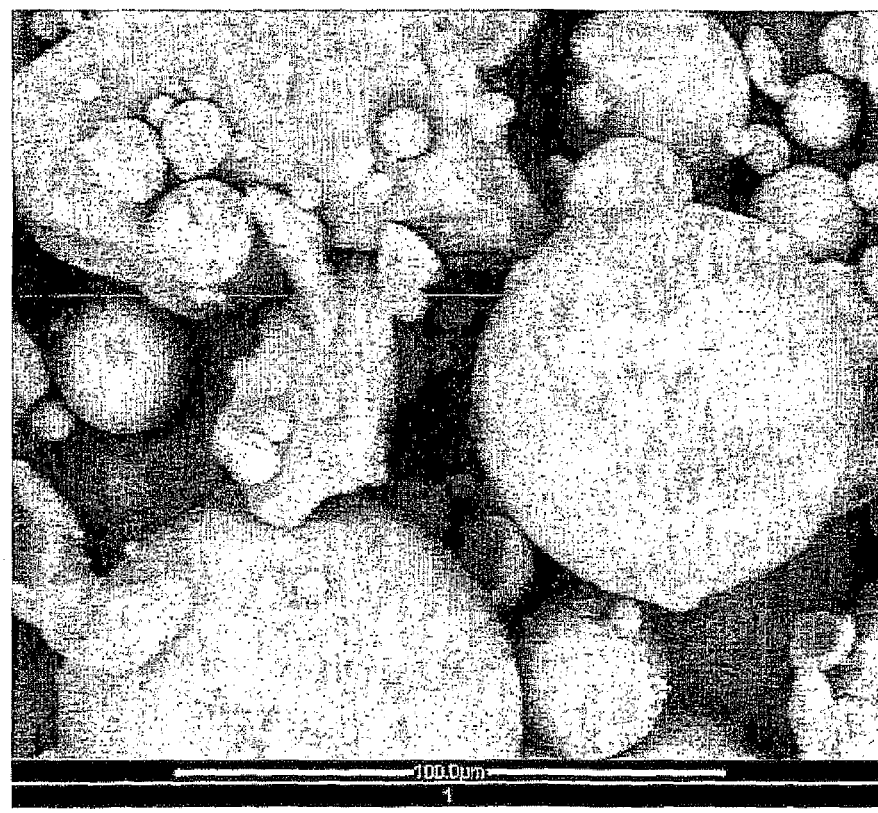
FIG. 5B represents a shot of a sample product of lactulose powder not using the process of the invention (enlarged 500 times). It is noted that the unitary particles have the same shape with a smooth surface state with particles of 30 to 100 microns.

The equipment used in this example is that of FIG. 1, i.e. a multi-stage spray-drying tower (1), the originality of the process of which is preferably to use the tower in single-stage modified configuration. The drops formed during the spraying of the lactulose solution are dried in the spraying chamber by hot air, the temperature of the incoming air being fixed at 120° C.

In this example, the cryogenic fluid is carbon dioxide.

A lactulose solution the lactulose purity of which is 70% expressed by weight of lactulose relative to the weight of dry material, and the concentration of which in dry solution extract is 65% expressed by weight of dry material relative to the weight of the solution, is transferred at a rate of 230 kg/h by a booster pump into a hot-water heat exchanger (2) to reach a temperature of 60° C. and undergoes continuous carbonation (3), the pressure of the carbonated mixture being 10 bars ($10^6$ Pa), before being sprayed using a high-pressure pump (4) at a pressure of approximately 160 bars ($1.6\times10^7$ Pa) via a pipe (5) with a single-fluid nozzle. Anti-agglomeration agent (6), preferably a colloidal silica, is continuously dosed at a level of 1% expressed by weight of silica to the weight of the dry solution extract, by injection close to the spraying zone.

The temperature of the fluidized bed is adjusted to keep the powder at a temperature of 21° C.

The temperature of the outlet air is chosen to be 76° C.; this supply of secondary air (8) is partially desaturated by a glycolated water counter-current cooling battery system, the air obtained having a residual humidity of 5 g of water per kg of air.

The air is recovered from the final powder under cyclone by choosing a dense phase conveying system and the powder is recovered by dense phase conveying.

The characteristics of the powders prepared according to this example are given in Table 2.

TABLE 2

| Moisture content of the finished product | 1.5% |
|---|---|
| Bulk density | 490 g/l |
| Flow (flowdex) | 20 |
| Water activity Wa | 0.173 |
| D(v, 0.5) | 71 μm |
| Average grain size by laser | |

Example 3

Multi-Stage Spray Drying in a Single-Stage Modified Configuration Tower

The equipment used in this example is that of FIG. 1, i.e. a multi-stage spray-drying tower (1), the originality of the process of which is preferably to use the tower in a modified single-stage configuration. The drops formed during the spraying of the lactulose solution are dried in the spraying chamber by hot air, the temperature of the incoming air being fixed at 120° C.

In this example, the cryogenic fluid is carbon dioxide.

A lactulose solution the lactulose purity of which is 70% expressed by weight of lactulose relative to the weight of dry material, and the concentration of which in dry solution extract is 70% expressed by weight of dry material relative to the weight of the solution, is transferred at a rate of 171 kg/h by a booster pump into a hot-water heat exchanger (2) to reach a temperature of 60° C. and undergoes continuous carbonation (3), the pressure of the carbonated mixture being 10 bars ($10^6$ Pa), before being sprayed using a high-pressure pump (4) at a pressure of approximately 114 bars ($1.14\times10^7$ Pa) via a pipe (5) with a single-fluid nozzle. Anti-agglomeration agent (6), preferably a colloidal silica, is continuously dosed at a level of 0.5% expressed by weight of silica to the weight of the dry solution extract, by injection close to the spraying zone.

The temperature of the fluidized bed is adjusted to keep the powder at a temperature of 18° C.

The temperature of the outlet air is chosen to be 76° C.; this supply of secondary air (8) is partially desaturated by a glycolated water counter-current cooling battery system, the air obtained having a residual humidity of 5 g of water per kg of air.

The final powder is stabilized by passing through a vibro-fluidizer equipped with two sections of heated air desaturated to 5 g of water per kg of air, the temperature of which over the first section is 44° C. and 33° C. over the second section. The powder is extracted at the outlet of the vibro-fluidizer and sieved.

The characteristics of the powders prepared according to this example are given in Table 3.

TABLE 3

| | |
|---|---|
| Moisture content of the finished product | 2.5% |
| Bulk density | 420 g/l |
| Flow (flowdex) | 5 |
| Water activity Wa | 0.276 |
| D(v, 0.5) | 300 µm |
| Average grain size by laser | |

The micro-granulated powder also has a grain size distribution centred on 350 µm, with 0 particles of a size greater than 800 µm and 5% of particles less than 80 µm, which gives the powder the excellent flowability characteristics allowing high-precision dosing operations without the presence of dust, thus limiting the risks of cross-contamination.

Example 4

Spray Drying in a W-Base Spraying Tower

In this example, the equipment used is a W-base tower the originality of the process of which is to use the W-base tower or two-stage tower preferentially in the configuration of a single-stage tower. The drops formed during the spraying of the lactulose solution are dried in the spraying chamber by hot air, the temperature of the incoming air being fixed at 106° C.

In this example, the cryogenic fluid is carbon dioxide.

A lactulose solution the lactulose purity of which is 70% expressed by weight of lactulose relative to the weight of dry material, and the concentration of which in dry solution extract is 66% expressed by weight of dry material relative to the weight of the solution, is transferred by a booster pump into a Joule effect preheater (2) of the Actijoule® type in order to reach a temperature of approximately 70° C. and undergoes continuous carbonation (3), the pressure of the carbonated mixture being 10 bars ($10^6$ Pa), before being sprayed using a high-pressure pump (4) at a pressure of approximately 40 bars ($4\times10^6$ Pa) via a pipe (5) with a single-fluid nozzle. Anti-agglomeration agent (6), preferably a colloidal silica, is continuously dosed at a level of 0.5% expressed by weight of silica to the weight of the dry solution extract, by injection close to the spraying zone.

The temperature of the fluidized bed is adjusted to keep the powder at a temperature of 25° C.

The temperature of the outlet air is chosen to be 75° C.; this supply of secondary air (8) is partially desaturated by a glycolated water counter-current cooling battery system, the air obtained having a residual humidity of 5 g of water per kg of air. The final powder is recovered under cyclone using a vacuum conveying system.

The characteristics of the powders prepared according to this example 4 are given in Table 4.

TABLE 4

| | |
|---|---|
| Moisture content of the finished product | 2.7% |
| Bulk density | 656 g/l |
| Flow (flowdex) | 7 |
| D(v, 0.5) | 60 µm |
| Average grain size | |

The values given for the flow index (flowdex) indicate a powder presenting excellent to good flow properties (see Example 1).

Example 5

Spray Drying in a W-Base Spraying Tower

In this example, the equipment used is a W-base tower the originality of the process of which is to use the W-base tower or two-stage tower preferentially in the configuration of a single-stage tower. The drops formed during the spraying of the lactulose solution are dried in the spraying chamber by hot air, the temperature of the incoming air being fixed at 106° C.

In this example, the cryogenic fluid is carbon dioxide.

A lactulose solution the lactulose purity of which is 70% expressed by weight of lactulose relative to the weight of dry material, and the concentration of which in dry solution extract is 66% expressed by weight of dry material relative to the weight of the solution, is transferred by a booster pump into a Joule effect preheater (2) of the Actijoule® type in order to reach a temperature of approximately 70° C. and undergoes continuous carbonation (3), the pressure of the carbonated mixture being 10 bars (10 Pa), before being sprayed using a high-pressure pump (4) at a pressure of approximately 40 bars ($4\times10^6$ Pa) via a pipe (5) with a single-fluid nozzle. Anti-agglomeration agent (6), preferably a colloidal silica, is continuously dosed at a level of 0.5% expressed by weight of silica to the weight of the dry solution extract, by injection close to the spraying zone.

The temperature of the fluidized bed is adjusted to keep the powder at a temperature of 25° C.

The temperature of the outlet air is chosen to be 75° C.; this supply of secondary air (8) is partially desaturated by a glycolated water counter-current cooling battery system, the air obtained having a residual humidity of 5 g of water per kg of air.

The final powder is collected under cyclone using a vacuum conveying system.

The characteristics of the powders prepared according to this example are given in Table 5.

TABLE 5

| | |
|---|---|
| Moisture content of the finished product | 3% |
| Bulk density | 484 g/l |
| Flow (flowdex) | 9 |
| D(v, 0.5) | 40 µm |
| Average grain size | |

Example 6

Multi-Stage Spray Drying in a Multi-Stage Configuration Tower

The equipment used in this example is that of FIG. 1, i.e. a multi-stage spray-drying tower (1), the originality of the process of which is preferably to use the tower in a multi-stage configuration. The tower is moreover equipped with a co-drying system at the top of the tower making it possible to ensure, at the same time, the continuous spraying of one or more components presenting known hygroscopicity criteria. The mixture formed by the mist of drops formed during the spraying of the lactulose solution and the cloud of solid particles blown out at the level of the spraying nozzle makes it possible to ensure the co-drying operation in the spray chamber using hot air, the temperature of the incoming air being fixed at 120° C.

In this example, the cryogenic fluid is carbon dioxide.

A lactulose solution the lactulose purity of which is 70% expressed by weight of lactulose relative to the weight of dry material, and the concentration of which in dry solution extract is 70% expressed by weight of dry material relative to the weight of the solution, is transferred at a rate of 171 kg/h by a booster pump into a hot-water heat exchanger (2) in order to reach a temperature of 60° C. and undergoes continuous carbonation (3), the pressure of the carbonated mixture being 10 bars ($10^6$ Pa), before being sprayed using a high-pressure pump (4) at a pressure of approximately 114 bars ($1.14 \times 10^7$ Pa) via a pipe (5) with a single-fluid nozzle. Anti-agglomeration agent (6), preferably a colloidal silica, is continuously dosed at a level of 0.5% expressed by weight of silica to the weight of the dry solution extract, by injection close to the spraying zone. A lactose powder is continuously dosed at a level of 30% expressed by weight of lactose to the weight of the dry solution extract at the same time, by injection close to the spraying zone.

The temperature of the fluidized bed is adjusted to keep the powder at a temperature of 18° C.

The temperature of the outlet air is chosen to be 76° C.; this supply of secondary air (8) is partially desaturated by a glycolated water counter-current cooling battery system, the air obtained having a residual humidity of 5 g of water per kg of air.

The final powder is stabilized by passing through a vibro-fluidizer equipped with two sections of heated air desaturated to 5 g of water per kg of air, the temperature of which over the first section is 44° C. and 33° C. over the second section. The powder is extracted at the outlet of the vibro-fluidizer and sieved.

The characteristics of the powders prepared according to this example are given in Table 6.

TABLE 6

| | |
|---|---|
| Moisture content of the finished product | 2% |
| Bulk density | 550 g/l |
| Flow (flowdex) | 5 |
| Water activity Wa | 0.28 |
| D(v, 0.5) Average grain size by laser | 350 μm |

The micro-granulated powder also has a grain size distribution centred on 375 μm, with 0 particles of a size greater than 800 μm and 5% of particles less than 80 μm, which gives the powder the excellent flowability characteristics allowing precision dosing operations without the presence of dust, thus limiting the risks of cross-contamination. Moreover, the powder presents a perfect homogeneity, each particle being uniformly constituted by the lactulose-lactose mixture at 70/30 in the same proportions as those initially defined during the spraying operations at the top of the tower.

Example 7

Multi-Stage Spray Drying in a Multi-Stage Configuration Tower, Associated with Co-Drying The equipment used in this example is that of FIG. 1, i.e. a multi-stage spray-drying tower (1), the originality of the process of which is preferably to use the tower in a modified multi-stage configuration. The tower is moreover equipped with a co-drying system at the top of the tower making it possible to ensure, at the same time, continuous spraying of one or more components presenting the known hygroscopicity criteria. The mixture formed by the mist of drops formed during the spraying of the lactulose solution and the cloud of solid particles blown out at the level of the spraying nozzle allows a co-drying operation to be ensured in the spray chamber using hot-air, the temperature of the incoming air being fixed at 120° C.

In this example, the cryogenic fluid is carbon dioxide.

A lactulose solution the lactulose purity of which is 70% expressed by weight of lactulose relative to the weight of dry material, and the concentration of which in dry solution extract is 70% expressed by weight of dry material relative to the weight of the solution, is transferred at a rate of 171 kg/h by a booster pump into a hot-water heat exchanger (2) in order to reach a temperature of 60° C. and undergoes continuous carbonation (3), the pressure of the carbonated mixture being 10 bars ($10^6$ Pa), before being sprayed using a high-pressure pump (4) at a pressure of approximately 114 bars ($1.14 \times 10^7$ Pa) via a pipe (5) with a single-fluid nozzle. Anti-agglomeration agent (6), preferably a colloidal silica, is continuously dosed at a level of 0.5% expressed by weight of silica to the weight of the dry solution extract, by injection close to the spraying zone. A mild lactoserum permeate powder is continuously dosed at a level of 30% expressed by weight of lactose to the weight of the dry solution extract at the same time, by injection close to the spraying zone.

The temperature of the fluidized bed is adjusted to keep the powder at a temperature of 18° C.

The temperature of the outlet air is chosen to be 76° C.; this supply of secondary air (8) is partially desaturated by a glycolated water counter-current cooling battery system, the air obtained having a residual humidity of 5 g of water per kg of air.

The final powder is stabilized by passing through a vibro-fluidizer equipped with two sections of heated air desaturated to 5 g of water per kg of air, the temperature of which over the first section is 44° C. and 33° C. over the second section. The powder is extracted at the outlet of the vibro-fluidizer and sieved.

The characteristics of the powders prepared according to this example are given in Table 7.

TABLE 7

| | |
|---|---|
| Moisture content of the finished product | 2% |
| Bulk density | 550 g/l |
| Flow (flowdex) | 6 |
| Water activity Wa | 0.18 |
| D(v, 0.5) Average grain size by laser | 350 μm |

The micro-granulated powder also has a grain size distribution centred on 375 μm, with 0 particles of a size greater than 800 μm and 5% of particles less than 80 μm, which gives the powder the excellent flowability characteristics allowing precision dosing operations without the presence of dust, thus limiting the risks of cross-contamination. Moreover, the powder presents a perfect homogeneity, each particle being uniformly made of the lactulose-lactoserum permeate mixture in a 70/30 ratio of lactulose/lactose in the same proportions as those initially defined during the spraying operations at the top of the tower.

Example 8

Measurement of the Hygroscopic Character of the Pulverulent Compositions of the Invention The hygroscopic and instability characters of the hygroscopic powders and in particular of lactulose is easily established following a test where a sample of produced powder (samples A and B) and the powders obtained from the invention (Examples 1 to 5) are placed in a small dish at ambient temperature and humidity (20° C. and 45% relative humidity).

The products of the prior art show a marked hygroscopicity with agglomeration after exposure for an extremely short time of 5 minutes leading to caking within the hour, in contrast to the products of the invention, which, according to the experimental conditions, lead either to stability with a slow agglomeration from 2 to 6 hours (powders of Examples 1, 2 and 5) or are totally stable (powders of Examples 3 and 4).

In the same way, the caking time is clearly improved. According to the experimental conditions, the powders present a delayed caking of 4 to 8 hours (powders of Examples 1, 2 and 5) or are totally stable (powders of Examples 3 and 4) after exposure for 72 hours.

Hygroscopicity and Caking Test

|  | Sample A | Sample B | Ex. 1 | Ex. 2 | Ex. 3 | Ex. 4 | Ex. 5 |
|---|---|---|---|---|---|---|---|
| Aggregation time (in minutes) | 2 | 3 | 120 | 120 | stable, no aggregation after 72 h | stable, no aggregation after 72 h | 360 |
| Caking time (in minutes) | 60 | 60 | 240 | 240 | stable, no caking after 72 h | stable, no caking after 72 h | 480 |
| % water recovery before caking | 0.7% | 0.6% | 3.2% | 2.1% | not applicable | not applicable | 1.2% |
| % water recovery after 8 h | 1.6% | 2.5% | 4.6% | 3.4% | 2.6% | 3% | 1.2% |
| % water recovery after 72 h | 1.9% | 3.7% | 4.1% | 4.1% | 3.2% | 3.3% | 0.9% |

The aggregation time is the time in which 1 to 2 grams of powder placed and distributed in a small aluminium dish (flat-bottomed cell 60 mm in diameter and 20 mm high) in an environment of 20° C. and 45% relative humidity in the air, the particles stick together.

Under the same operating conditions as for the aggregation time, the caking time is the time necessary for the aggregated particles together to remelt and form a solid.

The water take-up percentages by mass relative to the mass of the original sample are noted.

In the same way, the microphotographs (see FIGS. 5A, 5B, 6A, 6B and 7), carried out with a scanning electron microscope, clearly show the difference in quality of the products obtained and the specificity of the powders obtained from the invention, namely the ribbed and stretched particles during the transfer of gases with a particular mark at the level of the characteristic breakthrough point relating to evacuation of these gases from the sprayed powders of the "sunspot-type" particle.

The invention claimed is:

1. A process for the preparation of a non-hygroscopic pulverulent lactulose composition, comprising a stage of spray drying, without an atomization support, of an aqueous solution of lactulose and a cryogenic fluid, or a mixture of cryogenic fluids, said aqueous solution being obtained by dissolving said cryogenic fluid in an initial aqueous solution containing 60% to 80% by weight of lactulose relative to the total weight of dry matter wherein the cryogenic fluid is at a pressure from $10^5$ Pa to $20 \times 10^5$ Pa.

2. The preparation process according to claim 1, wherein the stage of spray drying is accompanied by a primary stabilization resulting from the cooling of the pulverulent composition obtained during the stage of spray drying.

3. The preparation process according to claim 2, wherein the cooling of the pulverulent composition obtained during the spray drying stage takes place within a temperature range lower than the glass transition temperature of the lactulose, and in that the water content of said pulverulent composition obtained on completion of said stage is less than 7%.

4. The preparation process according to claim 1, wherein the spray drying stage is preceded by a stage of simultaneous spraying of an anti-agglomeration agent and an aqueous solution of lactulose, and the cryogenic fluid used in the preparation process is a food-quality cryogenic fluid.

5. The preparation process according to claim 4, wherein the concentration of anti-agglomeration agent is less than 0.5% by weight of dry matter of the anti-agglomeration agent relative to the weight of dry extract of the non-hygroscopic pulverulent lactulose composition.

6. The preparation process according to claim 4, wherein the anti-agglomeration agent is selected from the group consisting of: colloidal silica, silicates, magnesium carbonate, calcium, talc and phosphate.

7. The preparation process according to claim 1, wherein the stage of spray drying is carried out with hot air at a temperature of 100° C. to 250° C.

8. The preparation process according to claim 1, wherein the initial aqueous solution containing lactulose is at a temperature of 50° C. to 85° C.

9. The preparation process according to claim 1, wherein the initial aqueous solution containing lactulose has a dry matter concentration of 20% to 80% by weight of dry matter relative to the weight of the initial aqueous solution.

10. The preparation process according to claim 1, wherein the aqueous solution of lactulose and the cryogenic fluid, is sprayed at a pressure of $2 \times 10^6$ Pa to $2 \times 10^7$ Pa.

11. The preparation process according to claim 2, wherein the stage of spray drying and primary stabilization resulting in a sprayed mixture is followed by a stage of secondary stabilization by cooling said sprayed mixture by secondary air which is partially dehydrated.

12. The preparation process according to claim 1, further comprising:
- a stage of secondary stabilization of the non-hygroscopic stabilized powder obtained at the outlet of the stage of spray drying and primary stabilization,
- wherein the non-hygroscopic pulverulent lactulose composition obtained at the outlet of the stage of spray drying and primary stabilization and the stage of secondary stabilization carried out in a spraying tower, is introduced into one or more cyclone(s).

13. The preparation process according to claim 1, wherein the non-hygroscopic pulverulent lactulose composition is recovered at the base of the spraying tower in microgranulated powder form, the average grain size of which can vary from 100 μm to 500 μm.

14. The preparation process according to claim 12, wherein the non-hygroscopic pulverulent lactulose composition is recovered at the outlet of one of the cyclones.

15. The preparation process according to claim 1, wherein the aqueous solution of lactulose and a cryogenic fluid is co-dried by spraying with a hygroscopic substance in powder form.

16. The preparation process according to claim 15, wherein the substance in hygroscopic powder form is chosen from organic products the average molecular mass of which is less than 1,000 Da.

17. The preparation process according to claim 16, wherein said organic products comprise at least 50% by weight of glucides.

18. The preparation process according to claim 17, wherein said glucides are selected from the group consisting of lactulose, fructo-oligosaccharides, fructose, saccharose, glucose and mixtures thereof, and polyols.

19. A continuous preparation process of a pulverulent lactulose composition according to claim 1, said process comprising the following stages:
- a stage of heating an initial aqueous solution containing lactulose at a temperature of 50° C. to 85° C., in order to obtain a heated initial aqueous solution,
- a stage of dissolution of a cryogenic fluid, in said heated initial aqueous solution, said cryogenic fluid being at a pressure comprised of $10^5$ Pa to $20 \times 10^5$ Pa, in order to obtain an aqueous solution of lactulose and a cryogenic fluid,
- a stage of simultaneous spraying of a anti-agglomeration agent and the aqueous solution of lactulose and a cryogenic fluid, in order to obtain a sprayed mixture,
- a stage of spray drying of said sprayed mixture with hot air at a temperature of 100° C. to 250° C., in order to obtain a hygroscopic powder, partially dried and not stabilized, and primary stabilization of said partially dried and not stabilized hygroscopic powder, in order to obtain a lactulose composition in the form of a non-hygroscopic stabilized powder,
- a stage of secondary stabilization of the non-hygroscopic stabilized powder obtained in the previous stage.

\* \* \* \* \*